United States Patent [19]

Chorev et al.

[11] Patent Number: 5,747,456
[45] Date of Patent: May 5, 1998

[54] CONTINUOUS LOW-DOSE ADMINISTRATION OF PARATHYROID HORMONE OR ITS AGONIST

[75] Inventors: Michael Chorev, Brookline; Michael Rosenblatt, Newton Centre, both of Mass.

[73] Assignee: Beth Israel Deaconess Medical Center, Boston, Mass.

[21] Appl. No.: 724,539

[22] Filed: Sep. 30, 1996

Related U.S. Application Data

[63] Continuation-in-part of Ser. No. 359,293, Dec. 19, 1994, abandoned.
[51] Int. Cl.⁶ .......................... C07K 14/00; A61K 51/00; G01N 33/534
[52] U.S. Cl. .................. 514/12; 514/21; 530/324
[58] Field of Search .......................... 514/12, 21; 530/324

[56] References Cited

U.S. PATENT DOCUMENTS

| | | | |
|---|---|---|---|
| 4,656,250 | 4/1987 | Morita et al. | 530/324 |
| 4,771,124 | 9/1988 | Rosenblatt et al. | 530/324 |

FOREIGN PATENT DOCUMENTS 0 477 885 A2  4/1992  European Pat. Off.

OTHER PUBLICATIONS

Dempster et al. Endocrinse Reviews, vol. 14(6), pp. 690–709, (1993).

Dempster et al., "Anabolic Actions of Parathyroid Hormone on Bone", Endocrine Reviews 14:690–709, 1993.

Hesch et al., "Increase of Vertebral Density by Combinaiton Therapy with Pulsatile 1–38hPTH and Sequential Addition of Calcitonin Nasal Spray in Osteoporotic Patients". Calcified Tissue Int'l 44:176–180, 1989.

Liu et al., "Human Parathyroid Hormone–(1–34) Prevents Bone Loss and Augments Bone Formation in Sexually Mature Ovariectomized Rats", Journal of Bone and Mineral Research 5:973–982, 1990.

Malluche et al., "Effects of long-term infusion of physiologic doses of 1–34 PTH on bone". The American Physiological Society, F197–F201, 1982.

Podbesek et al., "Effects of two treatment Regimes with Synthetic Human Parathyroid Hormone Fragment on Bone Formation & the Tissue Balance of Trabecular Bon in Greyhounds",Endocrinology 1000–1006, 1983.

Reeve et al., "Anabolic effect of human parathyroid hormone fragment on trabecular bone in involutional osteoporsis: a multicentre trial," British Medical Journal 1340–1343, 1980.

*Primary Examiner*—Cecilia J. Tsang
*Assistant Examiner*—P. Lynn Touzeau
*Attorney, Agent, or Firm*—William McGowan; John D. Conway; Fish & Richardson

[57] ABSTRACT

A method of promoting bone formation in a human patient, which includes the step of administering continuously to the patient parathyroid hormone or its agonist for a period of at least one month at a dosage between 10 and 400 units/24 hrs. Also disclosed are novel parathyroid hormone agonists.

21 Claims, No Drawings

CONTINUOUS LOW-DOSE ADMINISTRATION OF PARATHYROID HORMONE OR ITS AGONIST

CROSS REFERENCE TO RELATED APPLICATIONS

This application is a continuation-in-part of U.S. patent application Ser. No. 08/359,293, now abandoned, filed Dec. 19, 1994.

BACKGROUND OF THE INVENTION

Parathyroid hormone ("PTH") has been shown to effect a positive bone balance (reviewed in Dempster, D. W. et al., Endocrine Rev., 1993, 14, 690–709; Riggs, L., Amer. J. Med., 1991, 91 (Suppl 5B), 37S–41S). The mammalian parathyroid hormone is a polypeptide product of the parathyroid glands. The mature circulating form of the hormone is comprised of 84 amino acid residues. Parathyroid hormone-related protein ("PTHrP") is a 139 to 173 amino acid-protein with N-terminal homology to PTH. PTHrP shares many of the biological effects of PTH including binding to a common PTH/PTHrP receptor (Schipani E., et al., Endocrinology, 1993, 132, 2157–2165; Broadus, A. E., Steward, A. F., Parathyroid hormone-related protein: In: The Parathyroids, Bilezikian, J. P., Levine, M. A., Marcus R. Eds, Raven Press, NY, 1994, 259–294).

The general efficacy of daily acute administration of $PTH_{1-84}$ and $PTH_{1-34}$ has been demonstrated in young, adult, and aged rats of both sexes (Dempster, D. W. et al., Endocrine Rev., 1993, 14, 690–709; Gunness-Hey, M., et al., Metab. Bone Dis. & Rel. Res., 1984, 5, 177–181), as well as in other animal models, both normal and osteoporotic (Liu, C. C. et al., J. Bone Miner. Res., 1990, 5, 973–981; Podbesek, R., et al., Endocrinology, 1983, 112, 1000–1006). The anabolic effect of intermittently administered PTH is also observed in osteoporotic men (Slovik, D. M., et al., J. Bone Miner. Res., 1986, 1, 377–381) and women (Reeve, J., et al., Br. Med. J., 1990, 301, 314–318) and with concurrent antiresorptive therapy (Hesch, R-D., et al. Calcif Tissue Int, 1989, 176–180) suggesting that the process is not coupled to active resorption. $PTH_{1-34}$ is a synthetic amino-terminal fragment of $PTH_{1-84}$ (Tregear, G. W., et al., Endocrinology, 1973, 93, 1349–1353; Mosekilde, L., et al., Endocrinology, 1991, 129, 421–428).

The mechanism for the anabolic effect of intermittent PTH is not entirely clear (Dempster, D. W. et al., Endocrine Rev., 1993, 14, 690–709). The effect is dose-dependent within a defined dose range. There is increase in net calcium absorption from the intestine, and an increase in both calcium balance and calcium accretion into bone, with a corresponding increase in bone mass. This effect is also evident in the increase in trabecular bone forming surfaces and osteoblast number.

However, contrary to the demonstrated anabolic efficacy of daily subcutaneous injections of PTH, data from animal studies indicate that continuous administration (infusion) of the hormone either had no effect on bone growth or resulted in bone loss in dogs (Podbesek, R., et al., Endrocrinology, 1983, 112, 1000–1006; Malluche, H. H., et al., Am. J. Physiol., 1982, 242, F197–F202). Continuous administration of PTH has also been shown to inhibit osteoblast activity in humans. Simon, et al. (Simon, L. S., et al., J. Bone Miner. Res., 1988, 3, 241–246) examined the effects of intravenously infused $hPTH_{1-34}$ at a dose of 0.55 U/kg/hr (approximately 800 U over 24 hr) continuously for 24 hours in six osteoporotic subjects and two normal subjects. In all cases, serum levels of collagen type I, produced principally by osteoblasts, decreased within 16 hours of infusion, which also correlated with an increase in blood levels of ionized calcium.

SUMMARY OF THE INVENTION

The invention features a method of promoting bone formation in a human patient (e.g., a patient who suffers from osteoporosis). The method includes the steps of administering (e.g., transmucously, intravenously, transdermally, subcutaneously, via implantation, or via infusion) continuously to the patient PTH (mature form), PTHrP, or an agonist thereof for a period of at least one month (as long as the life time of the patient, if necessary) at a dosage between 10 and 400 units/24 hrs.

PTH and PTHrP include, but are not limited to, human PTH (hPTH), human PTHrP (hPTHrP), bovine PTH (bPTH), bovine PTHrP (bPTHrP), and rat PTH (rPTH). An agonist of PTH or PTHrP is a peptide which is a structural analog or fragment (preferably, an N-terminal fragment containing 50 or fewer amino acids) of a naturally occurring PTH or PTHrP and, like PTH and PTHrP, also capable of binding to PTH receptor and, thereby, promoting bone formation. Examples of such an agonist include, but are not limited to, $hPTH_{1-34}$ $NH_2$, $hPTH_{1-38}$ $NH_2$, $hPTH_{1-44}$ $NH_2$, $hPTH_{1-68}$ $NH_2$, $[Nle^{8,18}, Tyr^{34}]bPTH_{1-34}$ $NH_2$, $bPTH_{1-34}$ $NH_2$, $[Nle^{8,18},Tyr^{34}]bPTH_{1-34}$, $[Nle^{8,18},Phe^{22},Tyr^{34}]bPTH_{1-34}$ $NH_2$, $[Nle^{8,18},Arg^{19},Tyr^{34}]bPTH_{1-34}$ $NH_2$, $[Nle^{8,18},Arg^{21}, Tyr^{34}]bPTH_{1-34}$ $NH_2$, or $[Nle^{8,18},Arg^{19,21}, Tyr^{34}]bPTH_{1-34}$ $NH_2$. The symbol $NH_2$ denotes amidation of the carboxyl group (—CO.OH) of the C-terminal amino acid to form —$CO.NH_2$. The following publications disclose the sequences of PTH peptides: The Parathyroids Basic and Clinical Concepts, ed. John P. Bilezikian, 239–258 (Raven Press, NH 1994); Nissenson, R., et al., Structure & Function of the Receptor for Parathyroid Hormone and Parathyroid Hormone-Releasing Hormone, 3 Receptor 193–202 1993; Bachem California 1993–1994 Catalog (Torrance, Calif.); and Sigma Peptides and Amino Acids 1994 Catalog (St. Louis, Mo.). The following publications disclose the sequences of PTHrP peptides: Yasuda, et al., 264 J. Biol. Chem. 7720–7725 (1989); Schermer, D. T., Journal of Bone & Mineral Research 6:149–155 (1991) and Burtis, W. J., 38(11) Clinical Chemistry 2171–2183 (1992). More examples can be found in the following publications:

German Application 4203040 A1 (1993);
PCT Application 94/01460 (1994);
PCT Application 94/02510 (1994);
EP Application 477885 A2(1992);
EP Application 561412 A1 (1993);
PCT Application 93/20203 (1993);
U.S. Pat. No. 4,771,124 (1988);
PCT Application 92/11286 (1992);
PCT Application 93/06846 (1993);
PCT Application 92/10515 (1992);
U.S. Pat. No. 4,656,250 (1987);
EP Application 293158 A2 (1988);
PCT Application 94/03201 (1994);
EP Application 451,867 A1 (1991);
U.S. Pat. No. 5,229,489 (1993); and
PCT Application 92/00753 (1992).

Note that partial PTH agonists can also be used to practice the method of this invention. Examples of partial PTH agonists include, but are not limited to, N-terminal deletion analogs (e.g., $[Tyr^{34}]bPTH_{3-34}$ $NH_2$; see U.S. Pat. No. 4,771,124 (1988).

Preferred ranges of dosages include 10–300 units/24 hrs, 10–200 units/24 hrs, 10–100 units/24 hrs, 100–400 units/24 hrs, 200–400 units/24 hrs, and 300–400 units/24 hrs.

One unit of PTH, PTHrP, or an agonist thereof is defined by utilizing an in vitro cAMP accumulation assay with human SaOS-2 cells. Human SaOS-2 cells respond upon exposure to PTH, PTHrP, or an agonist thereof with a dose-dependent stimulation of cAMP accumulation. With $[Nle^{8,18},Tyr^{34}]hPTH_{1-34}\ NH_2$ as the reference standard analog (10,000 units/mg), a dose-response relationship can be generated using standard non-linear regression analysis. The relative potency for various PTH analogs (in units/mg) can be determined from the ratio of the $EC_{50}$ of the reference standard analog to that of the PTH analog. $EC_{50}$ is defined as the dose that evokes a half maximal response—cAMP accumulation herein. The detailed procedure for handling the cells, setting up the assay, as well as methods for cAMP quantitation, is described in Sistane, E., et al., Pharmacopeial Forum 20(3), 7509–7520 (1994).

If the administration is to be achieved via infusion, an ambulatory (e.g., MINIMED™ 404-SP, MiniMed Technologies, Sylmar, Calif.; Pharmacia Deltec CADD-MICRO MODEL™ S900, Pharmacia Deltec Inc., St. Paul, Minn.; or Disetronic Medical System's PANOMAT™, Plymouth, Minn.) or an implantable pump (e.g., MEDTRONIC SYNCROMED™, Medtronic, Inc., Minneapolis, Minn.) can be used.

Preferably, PTH, PTHrP, or an agonist thereof is administered as a sustained release formulation. As an example, the formulation may contain a homo- or a co-polymer prepared from lactic acid (D-isomer, L-isomer, or a racemate), glycolide, glycolic acid, caprolactone, or lactide.

Examples of suitable sustained release formulations can be found in the following publications:

U.S. Pat. No. 3,773,919 (1973);
U.S. Pat. No. 5,187,150 (1993);
U.S. Pat. No. 4,767,628 (1988);
U.S. Pat. No. 4,675,189 (1987);
U.S. Pat. No. 5,271,945 (1993);
U.S. Pat. No. 4,917,893 (1990); and
U.S. Pat. No. 3,887,699 (1975).

The sustained release formulations can be administered parenterally (e.g. subcutaneously, or intravenously) or by inhalation (e.g. using an aerosol delivery system; e.g., see WO93/00951 and WO94/07514).

In other embodiments, PTH, PTHrP, or an agonist thereof can be administered transmucously (e.g. nasal, vaginal, rectal) or transdermally (e.g. iontophoretic patch).

Also, if desired, a bone resorption inhibiting agent can also be administered during performance of the above described method. The term "inhibition of bone resorption" refers to prevention of bone loss, especially the inhibition of removal of existing bone either from the mineral phase and/or the organic matrix phase, through direct or indirect alteration of osteoclast formation or metabolism. Thus, the term "inhibitor of bone resorption" as used herein refers to agents that prevent bone loss by the direct or indirect alteration of osteoclast formation or metabolism. An example of suitable bone resorption inhibiting agents includes, but is not limited to, an estrogen, a bisphosphonate, sodium fluoride, a tamoxifen, vitamin D, and calcium. See U.S. Pat. No. 5,118,667 (1992).

The preferred dose and duration for practicing the above-described method varies depending upon the manner of administration, the age and the body weight of the subject and the condition of the subject to be treated, and ultimately will be decided by the attending physician. The formulations may conveniently be presented in unit dosage form and may be prepared by any of the methods well known in the art of pharmacy. All methods include the step of bringing the active ingredient(s) into association with the carrier which constitutes one or more accessory ingredients. In general, the formulations for tablets or powders are prepared by uniformly and intimately blending the active ingredient (e.g., hPTH) with finely divided solid carriers, and then, if necessary as in the case of tablets, forming the product into the desired shape and size.

The invention also features novel PTH or PTHrP agonists of the following formula:

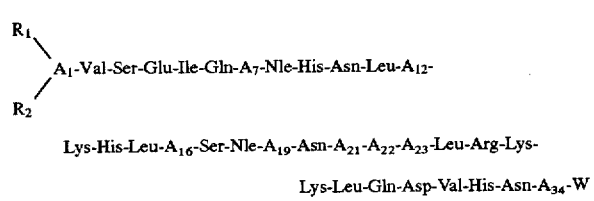

$$Lys-His-Leu-A_{16}-Ser-Nle-A_{19}-Asn-A_{21}-A_{22}-A_{23}-Leu-Arg-Lys-$$

$$Lys-Leu-Gln-Asp-Val-His-Asn-A_{34}-W$$

wherein:

$A_1$ is Ser or Ala;

$A_7$ is Leu or Phe;

$A_{12}$ is Gly, Aib, Ala, or D-Ala;

$A_{16}$ is Asn, Ser or Ala;

$A_{19}$ is Glu, Arg, Lys, Asp, Ser, Thr, Gln, Asn, or Ala;

$A_{21}$ is Val, Met, Arg, Lys, Glu, Asp, Ser, Thr, Gln, Asn, Leu, Ile, Nle, Ala, Phe, or p-X-Phe where X is OH, $CH_3$, $NO_2$, or a halogen;

$A_{22}$ is Glu, Asp, Phe, p-X-Phe where X is OH, $CH_3$, $NO_2$ or a halogen, Ser, Thr, Gln, Asn, Leu, Ile, Nle, Val, Ala, or Met;

$A_{23}$ is Trp, 1-Nal, or 2-Nal;

$A_{34}$ is Phe, or p-X-Phe where X is OH, $CH_3$, $NO_2$, or a halogen;

W is OH, $C_{1-12}$ alkoxy, $C_{7-20}$ phenylalkoxy, $C_{11-20}$ napthylalkoxy, or $NR_3R_4$; provided that when $A_{12}$ is Gly, $A_{19}$ is Glu, $A_{21}$ is Val, and $A_{22}$ is Gln, then $A_{23}$ must be 1-Nal or 2-Nal; and each of $R_1$, $R_2$, $R_3$, and $R_4$ is, independently, H, $C_{1-12}$ alkyl, $C_{7-10}$ phenylalkyl, or CO.E where E is $C_{1-12}$ alkyl, $C_{2-12}$ alkenyl, phenyl, naphthyl, or $C_{7-20}$ phenylalkyl; or a pharmaceutically acceptable salt thereof.

In the above formula, the N-terminus is at the left and the C-terminus at the right in accordance with the conventional representation of a polypeptide chain. Also, The symbol $A_1$, Val, $A_7$, or the like in a peptide sequence stands for an amino acid residue, i.e., =N—CH(R)—CO— when it is at the N-terminus or —NH—CH(R)—CO— when it is not at the N-terminus, where R denotes the side chain of that amino acid residue. Thus, R is —CH(CH$_3$)$_2$ for Val. Also, when the amino acid residue is optically active, it is the L-form configuration that is intended unless D-form is expressly designated. Further, the symbols Aib, 1-Nal, and 2-Nal herein are abbreviations for α-aminoisobutyric acid, 3-(1-naphthyl) alanine, and 3-(2-naphthyl)alanine, respectively.

Preferred groups of compounds covered by the above formula include (i) those where $A_1$ is Ala; $A_7$ is Phe; and $A_{16}$ is Ser; (ii) those where $A_{19}$ is Glu or Arg; and $A_{21}$ is Val or Arg; and (iii) those where $A_{22}$ is p-X-Phe where X is OH, $CH_3$, $NO_2$, or a halogen. Below are particularly preferred compounds: $[Nle^{8,18},Arg^{19},Tyr^{34}]bPTH_{1-34}\ NH_2$, $[Nle^{8,18},Arg^{21},Tyr^{34}]bPTH_{1-34}\ NH_2$, $[Nle^{8,18},Arg^{19,21},Tyr^{34}]bPTH_{1-34}\ NH_2$, and $[Nle^{8,18},Phe^{22},Tyr^{34}]bPTH_{1-34}\ NH_2$. Such compounds, as PTH or PTHrP agonists, can be used to promote bone formation in a manner described above.

Other features and advantages of the present invention will be apparent from the following description of the preferred embodiments, and also from the appending claims.

DESCRIPTION OF PREFERRED EMBODIMENTS

The synthesis, selection and use of PTH, PTHrP or agonists thereof which are capable of promoting bone formation are within the ability of a person of ordinary skill in the art.

For example, well-known in vitro or in vivo assays can be used to determine the efficacy of various PTH/PTHrP agonists to promote bone formation in human patients. For in vitro binding assays, osteoblast-like cells which are permanent cell lines with osteoblastic characteristics and possess receptors for PTH/PTHrP of either rat or human origin can be used. Suitable osteoblast-like cells include ROS 17/2 (Jouishomme, H., et al., Endocrinology, 1992, 130, 53–60), UMR 106 (Fujimori, A., et al., Endocrinology, 1992, 130, 29–60) and the human derived SaOS-2 (Fukuyama, S., et al., Endocrinology, 1992, 131, 1757–1769). The cell lines are available from American Type Culture Collection, Rockville, Md., and can be maintained in standard specified growth media. Additionally, transfected human embryonic kidney cells (HEK 293) expressing the human PTC receptor can also be utilized for in vitro binding assays. See Pines, et al., Endocrinology, 1994, 135, 1713–1716.

For in vitro functional assays, PTH and PTH-like agonist activities of peptide fragments or derivatives of parathyroid hormone or PTHrP can be tested by contacting a concentration range of the test compound with the cells in culture and assessing the stimulation of the PTH/PTHrP receptors. Receptor stimulation is evidenced by the activation of second messenger molecules coupled to the receptors, for example, a stimulation of cyclic AMP accumulation in the cell or an increase in enzymatic activity of protein kinase C, both of which are readily monitored by conventional assays (Jouishomme, H., et al., Endocrinology, 1992, 130, 53–60; Abou-Samra, A. B., et al., Endocrinology, 1989, 125, 2594–2599; Fujimori, A., et al., Endocrinology, 1991, 128, 3032–3039; Fukayama, S., Et al., Endocrinology, 1994, 134, 1851–1858; Abou-Samra, A. B., et al., Endocrinology, 1991, 129, 2547–2554; and Pines, et al., Endocrinology, 1994, 135, 1713–1716). Other parameters of PTH action include increase in cytosolic calcium and phosphoinositols, and biosynthesis of collagen, osteocalcin, and alteration in alkaline phosphatase activity.

PTH-like agonist activities of subfragments of PTH have been successfully analyzed by contacting peptides with rat kidney cells in culture and assessing cyclic AMP accumulation (Blind, E., et al., Clin. Endocrinol., 1993, 101, 150–155) and the stimulation of 1,25-dehydroxyvitamin $D_3$ production (Janulis, M., et al., Endocrinology, 1993, 133, 713–719).

The following specific embodiments are, therefore, to be construed as merely illustrative, and not limitative of the remainder of the disclosure in any way whatsoever. Furthermore, all of the references cited in this disclosure are incorporated by reference.

EXAMPLE 1

The PTH or PTHrP agonists of the invention were synthesized on an APPLIED BIOSYSTEMS™ 430A Automated Peptide Synthesizer (Applied Biosystems Inc., Foster City, Calif.) using version 1.40 of the software for NMP/HOBt Boc-based chemistry. The following side-chain protected amino acid derivatives were used in the course of the synthesis: N-Boc-Arg($N^G$-Tosyl)-OH, N-Boc-Asp(cycHx)-OH, N-Boc-Glu(OBzl)-OH, N-Boc-His(Bom)-OH, N-Boc-Lys(Cl-Z)-OH, N-Boc-Ser(Bzl)-OH, N-Boc-Thr(Bzl)-OH, N-Boc-Tyr(Br-Z)-OH, and N-Boc-Trp(N'-For)-OH.

Cleavage from resin with concomitant removal of the side-chain protecting groups of pMBHA-R-bound peptide was performed by liquid HF in the presence of 10% anisole (20 mL/g resin-bound peptide) 1 hr at 0° C. Low-high HF procedures shall be used for clevage from resin and deprotection for PTH agonists containing Trp. See Tam, et al., J. Am. Chem. Soc., 1983, 105, 6442. The resin-crude peptide mixture was washed with petroleum ether and ether. The dry resin-crude peptide mixture was extracted consecutively with 50% acetic acid and water. The combined washes were lyophilized. The lyophilized crude peptides were subjected to preparative RP-HPLC purification.

The full names for the abbreviations used above are as follows: Boc for t-butoxycarbonyl, For for formayl, cycHx for cyclohexyl, Cl-Z for 2-chlorobenzyloxycarbonyl, OBzl is O-benzyl, BOM for benzyloxymethyl, Bzl for benzyl, Br-Z for 2-bromo-benzyloxycarbonyl, $N^G$-Tosyl for tosyl at guanidyl site, and pMBHA-R for paramethoxybenzhydrylamine resin.

The crude peptides were purified on a WATERS DELTA PREP™ 4000 (Waters, Milford, Mass.), preparative HPLC system, connected to a PrepPack cartridge of Vydac™ C18 300A, 15–20 µm [47×300 mm] (Waters, Milford, Mass.) at a flow rate of 70 mL/min monitored at 220 nm. The analytical HPLC system included the following components: Waters 600E multisolvent delivery system, 490E programmable multiwavelength detector, 717 autosampler and a 747 data module. The samples were analyzed on a VYDAC™ C18 218TP5415 (150×4.6 mm, 5 µm), The Separation Group (Hesperia, Calif.) at a flow rate of 1 mL/min monitored at 220 nm. The solvent mixtures for both the analytical and preparative HPLC were: A: 0.1% TFA in $H_2O$, and B: 0.1% TFA in acetonitrile. The purity of the peptides and their derivatives exceeded 99% as determined from the analytical RP-HPLC.

The following four bovine PTH agonists were synthesized:

[Nle$^{8,18}$,Phe$^{22}$,Tyr$^{34}$]bPTH$_{1-34}$ NH$_2$ (Analog I);
[Nle$^{8,18}$,Arg$^{19}$,Tyr$^{34}$]bPTH$_{1-34}$ NH$_2$ (Analog II);
[Nle$^{8,18}$,Arg$^{21}$,Tyr$^{34}$]bPTH$_{1-34}$ NH$_2$ (Analog III); and
[Nle$^{8,18}$,Arg$^{19,21}$,Tyr$^{34}$]bPTH$_{1-34}$ NH$_2$ (Analog IV).

These four analogs were analyzed using HPLC (gradient of 30 min) and the results are shown in Table I below. For each solvent gradient, only the intitial and final percentages of B of the solvent (which consists of both A and B—see above for their compositions) are indicated.

TABLE I

| ANALOG | RETENTION TIME (min.) | SOLVENT GRADIENT (%) |
|---|---|---|
| I | 20.6 | 25–45 |
| II | 14.2 | 25–50 |
| III | 13.6 | 25–50 |
| IV | 17.1 | 20–50 |

The results of the amino acid analysis of the four analogs are shown in Table II below, which lists both calculated and found values.

TABLE II

| Amino Acid | | Analog I | Analog II | Analog III | Analog IV |
|---|---|---|---|---|---|
| Asx | Calcd. | 3.00 | 3.00 | 3.00 | 3.00 |
| | Found | 3.23 | 3.09 | 3.16 | 3.22 |

TABLE II-continued

| Amino Acid | | Analog I | Analog II | Analog III | Analog IV |
|---|---|---|---|---|---|
| Ser | Calcd. | 3.00 | 3.00 | 3.00 | 3.00 |
|  | Found | 2.75 | 2.54 | 2.48 | 2.86 |
| Glx | Calcd. | 4.00 | 4.00 | 5.00 | 4.00 |
|  | Found | 4.27 | 4.27 | 5.35 | 4.34 |
| Gly | Calcd. | 1.00 | 1.00 | 1.00 | 1.00 |
|  | Found | 1.03 | 1.08 | 1.01 | 1.07 |
| Ala | Calcd. | 1.00 | 1.00 | 1.00 | 1.00 |
|  | Found | 1.04 | 1.03 | 0.97 | 0.95 |
| Val | Calcd. | 3.00 | 3.00 | 2.00 | 2.00 |
|  | Found | 2.80 | 3.03 | 1.97 | 1.68 |
| Ile | Calcd. | 1.00 | 1.00 | 1.00 | 1.00 |
|  | Found | 0.99 | .096 | 0.91 | 0.81 |
| Leu | Calcd. | 4.00 | 4.00 | 4.00 | 4.00 |
|  | Found | 4.24 | 4.32 | 4.11 | 4.25 |
| Nle | Calcd. | 2.00 | 2.00 | 2.00 | 2.00 |
|  | Found | 1.61 | 1.50 | 1.94 | 2.19 |
| Tyr | Calcd. | 1.00 | 1.00 | 1.00 | 1.00 |
|  | Found | 1.15 | 1.06 | 1.01 | 1.10 |
| Phe | Calcd. | 2.00 | 1.00 | 1.00 | 1.00 |
|  | Found | 2.06 | 0.97 | 1.00 | 0.93 |
| His | Calcd. | 3.00 | 3.00 | 3.00 | 3.00 |
|  | Found | 2.85 | 3.03 | 2.93 | 2.64 |
| Lys | Calcd. | 3.00 | 3.00 | 3.00 | 3.00 |
|  | Found | 3.00 | 2.93 | 3.05 | 2.90 |
| Arg | Calcd. | 2.00 | 3.00 | 3.00 | 4.00 |
|  | Found | 1.97 | 3.20 | 3.11 | 4.04 |

Table III demonstrates the FAB (fast-atom bombardment) mass spectrometer analysis of the analogs.

TABLE III

| ANALOG | MEASURED | PREDICTED |
|---|---|---|
| I | 4106.8 | 4105.8 |
| II | 4114.7 | 4114.8 |
| III | 4146.4 | 4144.8 |
| IV | 4173.5 | 4172.8 |

EXAMPLE 2

SaOS-2 B10 cells were maintained in RPMI1640 medium supplemented with 10% fetal bovine serum (FBS) and 2 mM glutamine at 37° C. in a humidified atmosphere of 5% $CO_2$ in air. The medium was changed every three or four days, and the cells were subcultured every week by trypsinization.

SaOs-2 B10 cells were maintained for four days after they had reached confluence. The medium was replaced with 5% FBS RPS/1640 medium and incubated for 2 hrs at room temperature with $10 \times 10^4$ cpm mono-$^{125}$-I-[Nle$^{8,18}$,Tyr$^{34}$(3-I$^{125}$)]bPTH$_{1-34}$ NH$_2$ in the presence or absence of a competing tested PTH agonist. The cells were washed four times with ice-cold PBS and lysed with 0.1M NaOH, and the radioactivity associated with the cells was counted in a scintillation counter. Synthesis of the radiolabelled [Nle8,18, Tyr$^{34}$ (3-I$^{125}$)]bPTH$_{1-34}$NH$_2$ was carried out as described in Goldman M E et al., Endocrinology, 1988, 123, 1468–1475.

The binding assay was conducted on Analogs I–IV and Analog V (i.e., [Nle$^8$, Nle$^{18}$, Tyr$^{34}$]bPTH$_{1-34}$ NH$_2$). The $IC_{50}$'s (half maximal inhibition of binding of mono-$^{125}$I-[Nle$^{8,18}$,Tyr$^{34}$(3-I$^{125}$)]bPTH$_{1-34}$ NH$_2$) for the five tested analogs were calculated and shown in Table IV below:

TABLE IV

| ANALOG | $IC_{50}$ (nM) |
|---|---|
| I | 1.5 |
| II | 0.6 |
| III | 0.3 |
| IV | 0.3 |
| V | 1.5 |

EXAMPLE 3

The adenylate cyclase activity induced by each of Analogs I–V was also measured in SaOS-2 B10 cells as described previously (Rodan et al. 1983 J. Clin. Invest. 72;1511; Goldman et al. 1988 Endocrinology 123, 1468). Confluent SaOS-2 B10 cells in 24 wells plates were incubated 0.5 μCi[$^3$H]adenine (26.9 Ci/mmol, New England Nuclear, Boston, Mass.) in fresh medium at 37° C. for 2 hrs, and washed twice with Hank's solution. The cells were treated with 1 mM IBMX [isobutylmethylxanthine, Sigma, St. Louis, Mo.] in fresh medium for 15 min, and a tested PTH analog was added to the medium to incubate for 5 min. The reaction was stopped by the addition of 1.2M TCA followed by sample neutralization with 4N KOH. Cyclic AMP was isolated by the two-column chromatographic method (see Salomon et al. 1974 Anal. Biochem. 58;541). The radioactivity was counted in a scintillation counter (Liquid scintillation counter 2200CA, PACKARD, Downers Grove, Ill.). The $EC_{50}$'s (half maximal stimulation of adenylate cyclase) were calculated for the five PTH analogs and are shown below:

TABLE V

| ANALOG | $EC_{50}$ (nM) |
|---|---|
| I | 1.5 |
| II | 2.0 |
| III | 0.2 |
| IV | 0.5 |
| V | 2.0 |

EXAMPLE 4

In vivo bone anabolic activities of PTH/PTHrP agonists are tested by administering the peptide or a formulation containing the peptide into intact animals or an experimental animal model of osteopenia. The animal model can be osteoporosis in rats induced by ovariectomy (Hori, M., et al., Bone Miner., 1988, 3, 193–199; Geral, et al., J. Bone Miner. Res., 1989, 4, Suppl. 1, S303; Liu C-C. & Kalu, D. N., J. Bone Miner. Res., 1990, 5, 973–982; Mosekilde, L., et al., Endocrinol., 1991, 129, 421–428; Wronski, T. J., Yen C-F. Bone, 1994, 15, 51–58; Reviewed in Demster D. W., et al., Endocrine Rev., 1993, 14, 690–709).

The bone anabolic effects of the compound are determined following 12 to 60 days of treatment by assessing the change in bone mineral density by dual energy x-ray absorptiometry or dry weight of femurs or total ash weight (Hori, H., et al., Bone Miner., 1988, 3, 193–199; Hefti, E., et al., Clin. Sci., 1982, 62, 389–396). Increase in the rate of bone formation and mineralization are assessed using metabolic labels, e.g. tetracycline (Tam, C. S., et al., Endocrinology, 1982, 110, 506–512). Qualitative and quantitative evaluations of changes in trabecular/cortical bone volume and complexity are determined by standard histomorphometric methods (Wronski, T. J., Yet C-F, Bone, 1994, 15, 51–58;

Tam C. S., et al., Endocrinology, 1982, 110, 506–612; Podbesek, R., et al., Endocrinology 1983, 112, 1000–1006) of bone samples from control (untreated) and treated animals.

EXAMPLE 5

The anabolic efficacy of the PTH/PTHrP agonists are tested in humans (Review in Dempster D. W., et al., Endocrine Rev., 1993, 14, 690–709). To determine if continuous administration of hPTH$_{1-34}$ or its agonist is effective in promoting bone growth in humans, 30 post-menopausal women with established osteoporosis based on bone-density measurements are selected. A double-blind, placebo-controlled, randomized experiment is conducted where two groups of 15 women each are either placed on placebo treatment or continuous infusion of a defined dose of hPTH$_{1-34}$ (25 units to 400 units/24 hrs) using an infusion pump.

The patients prior to the study are subject to the following: complete health and physical examination, evaluation of the nutritional status (particularly of calcium intake and serum calcium), full analysis of biomarkers for bone-turnover (Riis, B. J., Amer. J. Med. 1993, 95 [Suppl 5A], 17s–21s; Delmas, P. D., Amer. J. Med., 1951, 91 [Suppl 5B], 59s–63s), radiology, bone mass measurements of vertebral and axial sites (Gerant, H. K., et al., Amer. J. Med., 1991, 91 [Suppl 5B], 49s–53s; Wasnich, R. D., Amer J Med, 1991, 91 [Suppl 5B], 54s–58s) and bone biopsy, to establish the baseline parameters for each individual. After one and three months of treatment, the patients are reevaluated for changes in serum calcium and biomarkers of bone turnover to determine the outcome of continuous hPTH$_{1-34}$ administration. When the biomarker analysis suggests an increase in osteoblast activity (e.g., increase in serum alkaline phosphatase and serum osteocalcin), the treatments are extended to twelve months, wherein bone mass measurements and bone biopsy further provide clear indication of bone growth in the population treated with continuous infusion hPTH$_{1-34}$.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of promoting bone formation in a human patient, said method comprising administering continuously to said patient PTH, PTHrP, or an agonist thereof for a period of at least one month at a dosage between 10 and 400 units/24 hrs.

2. A method of claim 1, wherein said dosage is 10–300 units/24 hrs.

3. A method of claim 1, wherein said dosage is 10–200 units/24 hrs.

4. A method of claim 1, wherein said dosage is 10–100 units/24 hrs.

5. A method of claim 1, wherein said dosage is 100–400 units/24 hrs.

6. A method of claim 1, wherein said dosage is 200–400 units/24 hrs.

7. A method of claim 1, wherein said dosage is 300–400 units/24 hrs.

8. A method of claim 1, wherein said agonist is hPTH$_{1-34}$ NH$_2$ or [Nle$^{8,18}$, Tyr$^{34}$]hPTH$_{1-34}$ NH$_2$.

9. A method of claim 1, wherein said agonist is bPTH$_{1-34}$ NH$_2$, [Nle$^{8,18}$,Tyr$^{34}$]bPTH$_{1-34}$ NH$_2$, [Nle$^{8,18}$,Phe$^{22}$, Tyr$^{34}$]bPTH$_{1-34}$ NH$_2$, [Nle$^{8,18}$,Arg$^{19}$,Tyr$^{34}$]bPTH$_{1-34}$ NH$_2$, [Nle$^{8,18}$,Arg$^{21}$,Tyr$^{34}$]bPTH$_{1-34}$ NH$_2$, or [Nle$^{8,18}$,Arg$^{19,21}$, Tyr$^{34}$]bPTH$_{1-34}$ NH$_2$.

10. A method of claim 1, wherein infusion is performed to administer said PTH, PTHrP, or an agonist thereof.

11. A method of claim 10, wherein said infusion is achieved with an ambulatory or implantable infusion pump.

12. A method of claim 1, wherein said PTH, PTHrP, or an agonist thereof is administered as a sustained release formulation.

13. A method of claim 12, wherein said sustained release formulation comprising a polymer prepared from lactic acid, caprolactone, glycolide, glycolic acid, or lactide.

14. A method of claim 1, further comprising the step of administering to said patient a bone resorption inhibiting agent.

15. A method of claim 14, wherein said bone resorption inhibiting agent is a bisphosphonate.

16. A method of claim 14, wherein said bone resorption inhibiting agent is a calcitonin.

17. A method of claim 14, wherein said bone resorption inhibiting agent is an estrogen.

18. A method of claim 12, further comprising the step of administering to said patient a bone resorption inhibiting agent.

19. A method of claim 18, wherein said bone resorption inhibiting agent is a bisphosphonate.

20. A method of claim 18, wherein said bone resorption inhibiting agent is a calcitonin.

21. A method of claim 18, wherein said bone resorption inhibiting agent is an estrogen.

* * * * *